(12) United States Patent
Gibson

(10) Patent No.: US 7,705,186 B2
(45) Date of Patent: Apr. 27, 2010

(54) PROCESS FOR THE PREPARATION OF SATURATED OR UNSATURATED PRIMARY FATTY AMINES

(75) Inventor: Scott Gibson, Dorset (GB)

(73) Assignee: Novagali Pharma SA, Evry (FR)

( * ) Notice: Subject to any disclaimer, the term of this patent is extended or adjusted under 35 U.S.C. 154(b) by 0 days.

(21) Appl. No.: 11/996,421

(22) PCT Filed: Jul. 21, 2006

(86) PCT No.: PCT/EP2006/064539

§ 371 (c)(1), (2), (4) Date: Jun. 3, 2008

(87) PCT Pub. No.: WO2007/010045

PCT Pub. Date: Jan. 25, 2007

(65) Prior Publication Data

US 2009/0105504 A1    Apr. 23, 2009

(30) Foreign Application Priority Data

Jul. 22, 2005   (EP) .................................. 05291572

(51) Int. Cl.
*C07C 209/28* (2006.01)
*C07C 209/84* (2006.01)

(52) U.S. Cl. ..................................................... 564/488

(58) Field of Classification Search .................. 564/488
See application file for complete search history.

(56) References Cited

U.S. PATENT DOCUMENTS 2,374,915 A * 5/1945 Bersworth .................... 554/51
5,840,985 A * 11/1998 Nepras et al. ............... 564/488

* cited by examiner

*Primary Examiner*—Brian J Davis
(74) *Attorney, Agent, or Firm*—Young & Thompson

(57) ABSTRACT

Process for the preparation of unsaturated and saturated primary fatty amines comprising the steps of chlorination, treatment by ammonia, reduction and purification.

7 Claims, 2 Drawing Sheets

Synthesis of oleylamine with the process according to the invention

PROCESS FOR THE PREPARATION OF SATURATED OR UNSATURATED PRIMARY FATTY AMINES

BACKGROUND OF THE INVENTION

1. Field of the Invention

The invention relates to a process for the preparation of saturated or unsaturated primary fatty amines.

2. Description of Related Art

The preparation of primary fatty amines from nitrites by hydrogenation of nitrites using catalysts has long been known. Thus in WO 03/070688 is disclosed an improvement of a method for producing primary amines by hydrogenating nitrites, which consists of using a hydrogenating catalyst modified ex situ with a pre-adsorbed alkali metal carbonate or alkali hydrogen carbonate such as $K_2CO_3$ or $KHCO_3$.

EP 1 050 527 discloses the preparation of unsaturated and saturated primary amines (e.g., oleylamine) in high yield and with clear color by hydrogenating nitrites (e.g., oleyl nitrile) in the presence of a Raney catalyst containing 90-96% Ni, 3-9% Al and 0.5-3% Mo. Alkylene oxides (e.g., ethylene oxide) may also be added to the reaction mixture to obtain the polyalkylene oxide adducts (e.g., stearylamine ethylene oxide adduct) of the primary amines.

EP 490 382 discloses the preparation of saturated primary fatty amines by a two-step hydrogenation of unsaturated fatty nitrites. The first hydrogenation produces unsaturated fatty amines, which are then hydrogenated in a second step to the saturated amines. The hydrogenations are carried out in the presence of 0.1-10 weight % of a Ni or Co catalyst at 80-160° C. in the presence of $NH_3$. The first hydrogenation is carried out at 10-50 bar and the second hydrogenation is carried out at 1-40 bar. Thus, oleonitrile with iodine number of 88 was converted in two steps to stearyl amine with iodine number of 4 using Raney Ni as catalyst.

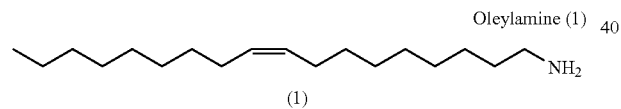

Oleylamine (1)

(1)

is used for the synthesis of organic chemicals and surfactants, used as a corrosion inhibitor, detergent, or floating agent, fabric softener, antistatic agent, germicide, insecticide, emulsifier, dispersant, anticaking agent, lubricant and water treatment agent. It also may be incorporated in the emulsion droplets resulting from the aqueous dilution of conventional SEDDS (Self Emulsifying Drug Delivery System) formed by traditional oil/non-ionic surfactant blend; said systems carry some negative charge, possibly provided by free fatty acids present in the mixture. Incorporation of a small amount of a cationic lipid, oleylamine [2.5-3%] into such a system reversed the charge nature, leading to the formation of emulsion droplets, which exhibit a positive zeta-potential value of about 35-45 mV. Such emulsions are disclosed in WO 96/33697.

In the case of the hydrogenation of unsaturated fatty acid nitriles to saturated primary fatty amines using nickel catalysts or cobalt catalysts, the opinion generally prevails that in addition to the use of ammonia, a relatively high pressure and/or a high temperature must also be employed, so that not only is the nitrile group hydrogenated to the primary amino group, but the olefinic double bonds are also hydrogenated.

On the basis of the prior art, it appears therefore that the hydrogenation of olefinic double bonds in the unsaturated primary fatty amine requires high pressures and/or high temperatures, and also the presence of a relatively large amount of ammonia.

Moreover, in the case of oleylamine, hydrogenation of the nitrile approach would result in saturation, or at the very least to isomerisation of the internal C—C double bond, both of which are undesirable.

BRIEF SUMMARY OF THE INVENTION

It is accordingly the object of the invention to provide a process by means of which the preparation of primary fatty amines may be achieved simply, in high yield and with minimal levels of impurities.

The process according to the invention for the preparation of unsaturated and saturated primary fatty amines comprising the steps of:
(a) chlorination of the corresponding acid by treatment with neat thionyl chloride in dichloromethane at reflux temperature, to obtain a solution of corresponding chloride in dichloromethane,
(b) addition of the chloride solution of step a) to a solution of liquid ammonia in dichloromethane at a temperature comprised between 0 and 10° C. to yield the corresponding amide,
(c) reduction of the amide to amine by treatment with lithium aluminium hydride in tetrahydrofuran, followed by extraction of amine by t-butyl methyl ether,
(d) purification of amine of step c) by treatment in solution in t-butyl methyl ether by hydrochloric acid followed by treatment by acetonitrile to yield amine hydrochloride, and optionally,
(e) treatment of amine hydrochloride of step d) by t-butyl methyl ether and a base to yield amine as a free base.

BRIEF DESCRIPTION OF THE DRAWING

The process is illustrated in FIG. 1 for oleylamine and in the example 1 to 3.

Figure 1:
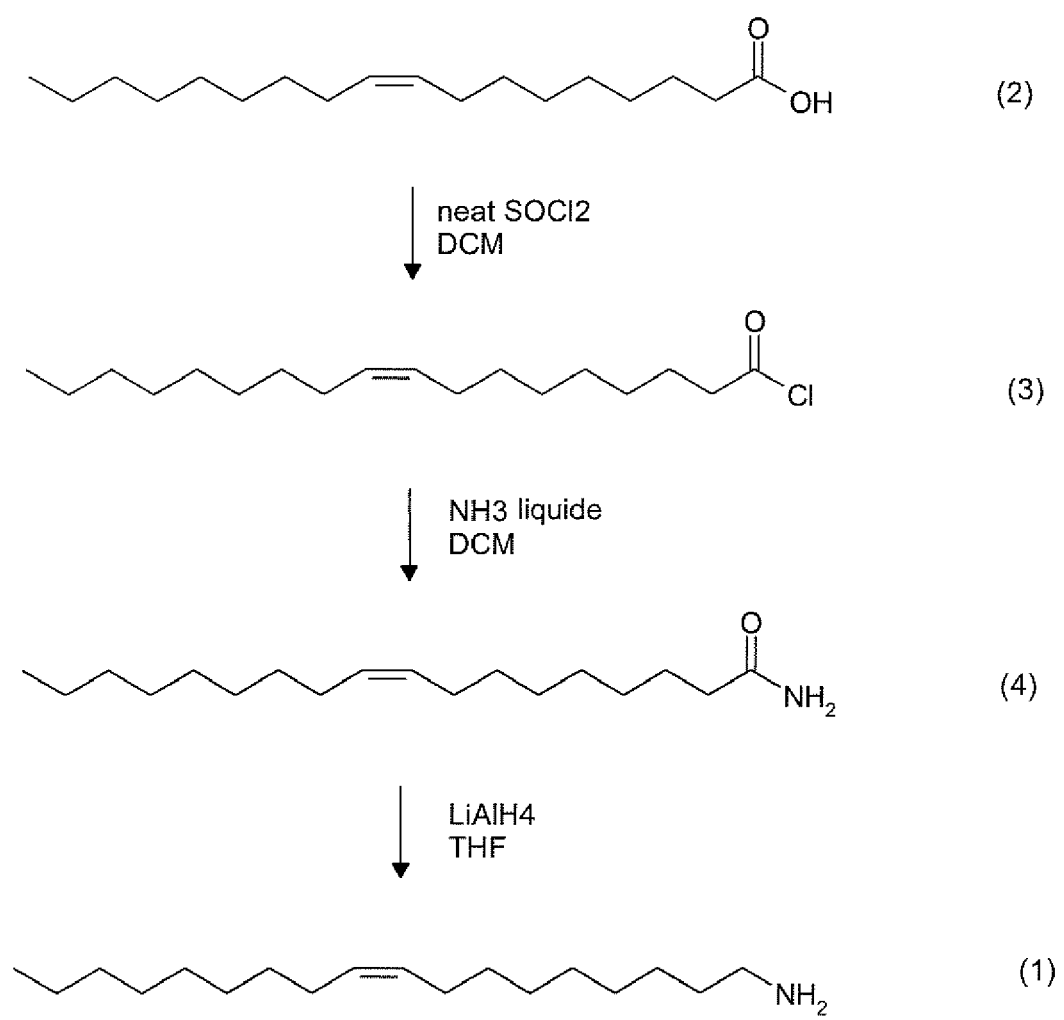

According to the invention, primary saturated and unsaturated fatty amines are amines comprising 4 to 30 carbons atoms, advantageously 15 to 24 carbons atoms, unsaturated amines being allowed to comprise one or more double bonds. Isomers and salts thereof are also part of the invention.

Preferred amines are oleylamine, stearylamine and their respective isomers, like for example elaidylamine, trans-isomer of oleylamine.

Advantageously, the acid used in step a) is oleic acid, more advantageously oleic acid with more than 99% purity and the amine obtained according to said process is oleylamine.

In step a) the transformation of acid into amide by neat thionyl chloride in dichloromethane avoids isomerisation by lowering the boiling point (40° C. versus 108° C. for toluene). The conversion of the acid to the chloride is between 97 and 100%. When 99% oleic acid is used, the reaction of oleoyl chloride to yield oleylamide proceeds well to yield product which is consistently >98% purity. The level of hydrolysis is not greater that 10%, and therefore a reaction yield of 80-85% can be realistically achieved on this step. The obtained product may be used directly in the next step.

The inventors found that ammonia gas is significantly soluble in dichloromethane to allow preparation of an anhydrous solution of ammonia to be prepared. This allowed reaction of chloride with ammonia to give amide with minimal hydrolysis. In step b) the chloride solution is preferably introduced directly into ammonia solution by means able to significantly reduce the emissions of ammonium chloride, like a dosage pipe. The reaction mixture is then quenched with any technique known from the one skilled in the art, for example with 5M hydrochloric acid solution. The quantity of acid required is optimised to effect complete dissolution of precipitated ammonium chloride, and hence results in acceptable phase separation. In an advantageous mode, the quantity of acid has been optimised at 20 liters per kilo of oleic acid substrate processed. After separation of the acidic aqueous layer, residual oleic acid is removed as the sodium salt by washing with a basic solution like 1M sodium carbonate solution. The number and volume of washes required is dependent of the level of acid present and is well in the hand of the one skilled in the art. After the basic wash, the aqueous layer is back-extracted into dichloromethane. The amide solution in dichloromethane is then washed three times with water to removal residual inorganic salts. To evaluate the yield of product obtained, the amide was isolated by evaporation to dryness to obtain a white crystalline solid. A consistent yield range of 85-95% may be achieved.

In step c, to cleanly reduce the amide to the amine, 1 to 3, advantageously 2.5 equivalents of 1M lithium aluminium hydride are used. The medium is stirred at 50-60° C. during 1 to 3 hours. After reaction of oleylamide with lithium aluminium hydride, the reaction mixture is quenched after cooling of the reaction medium, with any technique known from the one skilled in the art, for example with 30 to 40% aqueous sodium hydroxide solution, advantageously with 32% aqueous sodium hydroxide solution. The use of t-butyl methyl ether (TBME) instead of toluene as the extraction solvent avoids residual solvent issues in the final product. The crude amine is obtained in excellent yield and purity.

Purification of oleylamine via isolation of oleylamine hydrochloride is the important part of the process according to the invention. Due to the very unusual solubility properties of oleylamine and its ammonium salts, the inventors found that a solution of oleylamine in t-butyl methyl ether could be reacted to the hydrochloride salt by reaction of aqueous hydrochloric acid to give a monophasic solution. This solution could then be precipitated by addition to acetonitrile without need for solvent replacement. The precipitation is extremely tolerant to high levels of water or t-butyl methyl ether giving a very efficient product yield of a white crystalline solid with all non-amine impurities rejected. In an advantageous embodiment, aqueous hydrochloric acid is a 30 to 37% hydrochloric acid solution.

In another advantageous embodiment of the invention, oleylamine represents in step d) 10 to 30% of the reaction medium, more advantageously 15 to 25% of the reaction medium.

In said step d) high temperature, high vacuum distillation, which would have been time consuming and energy inefficient on a large scale, are avoided. Purification via the ammonium salt effectively reduces any non-amine organic impurities to an acceptable limit ($\leqq 0.05\%$ by GC). Precipitation from acetonitrile by TBME avoids the necessity for complete solvent replacement, which is time-consuming on scale. By use of hydrochloric acid (which is used earlier in the process during the amidation quench) no new reagents have been introduced to the process. The return of oleylamine from the hydrochloride was nearly quantitative (95-97%) upon evaporation of the organic phase and the purified product was found to be near 99.5% oleylamine by GC or by acid titration.

The four steps were performed as one process, with none of the intermediates being isolated.

EXAMPLE 1

Synthesis of Oleylamine 1.1. Preparation of Oleoyl Chloride

Oleic acid (20.00 kg) (±1%) and dichloromethane (212.00 kg, 160.00 L) (±2%) are charged to the reactor. The stirrer is started. The volume of the medium is about 180 L. The resultant solution is heated to reflux (39-41° C.) during about 1 hour.

To the refluxing solution, a solution of thionyl chloride (10.11 kg) (±1%) is added over 0.75 to 1.25 hours. The volume of the medium is about 186 L.

The reaction is stirred out at reflux (39-41° C.) for 2.75 to 3.25 hours and the yellow coloured acid chloride solution is cooled to 15-25° C. and stored under nitrogen for use in the subsequent reaction. The solution should be processed without undue delay.

1.2. Preparation of Oleylamide

Dichloromethane (600.00 kg, 452.83 L) (±2%) is charged to the reactor and the stirrer is started. The contents of the reactor are cooled to 0-5° C. Ammonia (48.00 kg) (±2%) is charged as a liquid over 1.5 to 2.0 hours. To the ammonia solution, the oleoyl chloride solution is added over 1.25 to 1.75 hours at 0-10° C. The volume of the medium is about 580 L.

The reaction mixture is stirred out at 0-10° C. for 1.75 to 2.25 hours. A sample of the reaction mixture is analysed by HPLC (quench sample into MeOH). If the reaction has not proceeded to completion (limit 0.5% acid chloride as the methyl ester by HPLC), then the reaction mixture is stirred out for a further 0.75 to 1.25 hours and resample.

At the end, the reaction is quenched by addition of 5M hydrochloric acid solution (400.0 L) (±2%). Ammonium chloride formed will dissolve to give two separable layers. The volume of the medium is about 980 L. The lower dichloromethane layer is separated and retained and the upper aqueous layer is removed and discarded. The dichloromethane layer is washed with 1M sodium carbonate solution (2×80 L). The maximum approximate volume is 740 L. The combined carbonate washes are extracted and back-extracted with dichloromethane (106.00 kg, 80.00 L) (±2%). The combined dichloromethane layers are washed with water (3×100 L) (±2%). The maximum approximate volume is 760 L.

The dichloromethane solution is distilled to minimum stirred volume at atmospheric pressure and then tetrahydrofuran is charged (426.72 kg, 480.00 L) (±2%) while continuing the distillation until a pot temperature of >65° C. is obtained; the distillate is <1% dichloromethane by Gas Chromatography. If level of dichloromethane is >1% distillation is continued with addition of tetrahydrofuran until specification is met.

The tetrahydrofuran solution is concentrated to ~10% w/w (~220.0 L), removed from the reactor and stored for use in the subsequent reduction reaction.

1.3. Preparation of Oleylamine 1.0 M lithium aluminium hydride solution is charged in tetrahydrofuran (160.20 kg, 177.02 L) (±1%) to the reactor and the stirrer is started. The reactor contents are heated to 50-60° C. To the lithium aluminium solution the amide solution in tetrahydrofuran is charged over 1.75 to 2.25 hours, maintaining the reaction temperature between 50-60° C. The approximate volume is 397.0 L. The reaction is stirred at 50-60° C. for 1.75 to 2.25 hours. The reaction mixture is sampled and analysed by gas chromatography GC (quench sample into excess 32% NaOH solution and remove lower aqueous layer). The limit is 0.5% oleylamide by GC. If the reaction has not proceeded to completion, the medium is stirred-out for a further 0.75 to 1.25 hours and resampled. The reaction mixture is cooled to 15-25° C.

Into the larger paired reactor 32% w/w sodium hydroxide solution is charged in water (800.00 Kg) (±5%). Approximate volume is 595 L. The reaction mixture is charged to the sodium hydroxide solution via the charge vessel over 1.0 to 2.0 hours, maintaining the temperature of the reactor contents below 40° C. Approximate volume is 995 L.

T-butyl methyl ether (148.00 kg, 200.00 L) (±2%) is charged to the reactor and stirred for 0.25 to 0.75 hours. The mixture is allowed to separate. Approximate volume is 1 195 L.

The lower aqueous layer is separated and retained. The upper organic layer is removed and retained. The aqueous layer is re-extracted with t-butyl methyl ether (74.00 kg, 100.00 L) (±2%). Approximate volume is 670 L. The combined organic layers are washed with deionised water (3×200 L) (±5%). Approximate maximum volume is 520 L.

The resultant organic solution is concentrated to give a ~15-20% w/v solution of crude product in t-butyl methyl ether (containing ~15 Kg of oleylamine). Approximate volume is 90 L.

1.4. Purification of Oleylamine

To the stirred crude amine solution in TBME (~90 L) pf step 1.3, 6.7 Kg (1.2 eq) (±2%) of concentrated (37%) hydrochloric acid are added via dosing pump, over 15-30 minutes, at a temperature of 20-30° C. (exothermic addition). Approximate volume is 95 L. The clear monophasic solution is stirred for at least 30 minutes at 20-30° C. and acetonitrile (225.0 L, 176.85 Kg) (±5%) is charged to the paired reactor. The hydrochloride salt solution is charged to the acetonitrile over 30-60 minutes to form a white precipitate. Approximate volume is 320 L.

The precipitate is cooled to 0-6° C., hold for at least 1 hour and filtered. The cake volume is about 90 L. The precipitate is washed with 2×35 L of chilled acetonitrile and the solid is dried at 25-30° C. to constant weight (DSC performed).

The dried solid is transferred back into the reactor and 10 weight volumes (~135 L, 100 Kg) of TBME are added. The reaction medium is stirred until a solution is obtained. Approximate volume is 150 L.

2. Equivalents (~50.5 L) of 2M sodium hydroxide solution in water are added over 15-30 minutes at 15-25° C. (addition is slightly endothermic). Approximate volume is 200 L and the biphasic mixture is stirred for at least 1 hour at 15-25° C. and allows separating. The lower aqueous layer is removed and discarded. The organic solution is washed with water (2×35 L), azeo-dried by distillation at atmospheric (b.p. TBME 58° C.) and then concentrated to dryness under full house vacuum until residual levels of TBME are within ICH guidelines by headspace GC.

EXAMPLE 2

Preparation of Elaidylamine Reference Marker 2.1. Preparation of Elaidylamide

To a 500 $cm^3$ round-bottomed flask fitted with magnetic stirrer, temperature probe, nitrogen inlet and a 100 $cm^3$ dropping funnel was charged elaidic acid (99%) (45.0 g, 0.159 mol) and dichloromethane (360 $cm^3$). The resultant solution was heated to reflux (39-41° C.) and thionyl chloride (22.7 g, 1.2 eq.) added over 5 minutes between 39-41° C.

The reaction mixture was heated at reflux for 2.0 hours, sampling the mixture at hourly intervals (sample quenched into anhydrous methanol, shaken well, and stored at ambient for >1 hour before submitted to analytical development for analysis) after which time the reaction was shown to be 99.7% complete by HPLC (acid chloride derivatised to Me ester).

To a 2-liter flange-neck flask fitted with overhead stirrer, nitrogen inlet, condenser (with silica drying tube) and a gas sparging inlet was charged dichloromethane (1350 g). The solvent was cooled to 0-10° C. and then ammonia (108 g) was charged as a gas via the sparging inlet over 32 minutes, maintaining the reaction mixture between 0-10° C. The acid chloride solution in dichloromethane was then added to the stirred ammonia solution via a 500 $cm^3$ dropping funnel over 25 minutes, maintaining the reaction temperature below 10° C. The resultant pink-coloured suspension was allowed to stir at 0-10° C. for 2 hours, after which time the reaction was shown to be complete by HPLC, but a high level of hydrolysis to elaidic acid had occurred (66.08% elaidylamide, 32.84% elaidic acid).

The reaction mixture was quenched by the addition of 5M hydrochloric acid (900 $cm^3$)—unlike the oleylamide reaction, two clear layers were not obtained, so an additional 100 $cm^3$ of 5M hydrochloric acid was added. The mixture was allowed to separate overnight, after which time satisfactory phase separation was achieved. The lower organic phase was separated and washed with 1M sodium carbonate solution (2×180 $cm^3$). The level of residual elaidic acid was found to be 4.19% by HPLC, so an additional 1M sodium carbonate wash (360 $cm^3$) was performed, which reduced the level of acid to 0.39%. The combined carbonate washes were then back-extracted with dichloromethane (180 $cm^3$) which formed a slow-separating emulsion. The combined organic extracts were washed with water (3×360 $cm^3$) (final water wash pH=8.9), and the resultant amide solution evaporated to yield elaidylamide as a white crystalline product (24.1 g, 54).

This material was shown to be 98.33% elaidylamide, 0.38% elaidic acid and 0.35% oleylamide by HPLC.

2.2. Reduction of Elaidylamide (SG/197/55)

To a 500 $cm^3$ round-bottomed flask fitted with magnetic stirrer, nitrogen inlet, temperature probe, condenser and a 100 $cm^3$ pressure-equalized dropping funnel, was charged 1.0 M lithium aluminium hydride solution in tetrahydrofuran (196 $cm^3$, 2.5 eq.). Since elaidylamide was virtually insoluble in tetrahydrofuran, the amide (22.0 g) was added to the lithium aluminium hydride solution as a slurry in a 4:1 mixture of THF/TBME (200 $cm^3$ THF+50 $cm^3$ TBME) to the lithium aluminium hydride solution over ~25 minutes at 45-55° C., followed by a wash of TBME (50 $cm^3$).

The resultant mixture was stirred at 44-55° C. for 3 hours, after which time the reaction was found to be 98.4% complete by GC (slower reaction rate due to slightly lower reaction temperature used, which was dictated by the TBME content). The reaction was quenched by addition to 32% w/w sodium hydroxide solution (1100 g) over 20 minutes, maintaining the reaction temperature below 40° C. An additional 150 cm$^3$ of TBME was charged and the mixture stirred for 10 minutes (to dissolve residual inorganic salts), transferred to a separatory funnel and allowed to separate. The lower aqueous layer was separated and re-extracted with TBME (150 cm$^3$). The combined organic extracts were then washed with water (3 ×350 cm$^3$) (final water wash pH=9.5) and the resultant amine solution evaporated to yield crude elaidylamine as a yellow oil (19.7 g, 94.2%) which solidified upon cooling to yield a white crystalline solid.

GC Analysis: 96.36% elaidylamine, 1.55% elaidylamide, 0.46% unknown, presumably elaidyl alcohol.

2.3. Purification of Elaidylamine (SG/197/58)

To a 250 cm$^3$ round-bottomed flask fitted with magnetic stirrer, nitrogen inlet, temperature probe, condenser and a 100 cm$^3$ pressure-equalized dropping funnel, was charged crude elaidylamine (17.0 g, 63.6 mmol) and t-butyl methyl ether (85 cm$^3$, 5 volumes). The substrate did not dissolve, so an additional 85 cm$^3$ of TBME was added. Although a solution was not obtained, the resultant slurry was deemed adequate for further processing. The stirred slurry was treated with 37% hydrochloric acid (7.6 g, 1.2 eq.). During this addition the slurry became very thick and difficult to stir, suggesting that elaidylamine hydrochloride is poorly soluble in TBME. Water (100 cm$^3$) was therefore added which eventually yielded a clear monophasic solution. The hydrochloride was then precipitated by addition to excess acetonitrile (750 cm$^3$). The resultant suspension was cooled to 0-5° C., stirred for 30 minutes, filtered and washed with cold acetonitrile (2×200 cm$^3$). The solid was then dried under vacuum at 30-35° C. to yield elaidylamine hydrochloride as a white crystalline powder (12.1 g, 63%) The hydrochloride (12.1 g) was then slurried in TBME (180 cm$^3$ 15 volumes) and treated with 2M sodium hydroxide solution (40 cm$^{-3}$, 2 eq.). During the addition the solid dissolved to give a bi-phasic solution which was stirred overnight. The mixture was then transferred to a separating funnel, the lower aqueous layer removed, and the organic phase washed with water (2×50 cm$^3$). The resultant product solution was then evaporated to yield elaidylamine as clear oil, which solidified upon cooling to room temperature (10.7 g, 100% from hydrochloride, 63% from crude amine).

Preliminary analysis performed by analytical development showed that the material was 99.58% elaidylamine, with 0.08% residual elaidylamide present by GC. The melting point of the product was shown to be 30.5° C. by Differential Scanning Calorimetry (DSC).

The product was qualified as a reference marker with the following main characteristics gathered in Table 1 below:

TABLE 1

Analysis of Elaidylamine Reference Marker

| Test | Specification | Result Batch U12542 |
|---|---|---|
| Appearance | Report | White crystalline solid |
| FT-IR | Conforms to Structure | Conforms to Structure |
| $^1$H NMR | Conforms to Structure (Report any unknown or unrelated signals) | Conforms to Structure |
| $^{13}$C NMR | Conforms to Structure | Conforms to Structure |
| Mass Spectrometry | M. Wt. = 267.49 | Conforms |
| Purity (GC) | Report | 100.00% |
| Microanalysis | 80.82% C; 13.94% H; 5.24% N | 80.72% C (99.88%); 14.16% H (101.58%); 5.18% N (98.85%) |
| Karl Fischer | Report | 0.33% |
| Sulphated Ash | Report | 0.11% |
| Titration | Report | 99.42% |
| Residual Solvents (GC) | | |
| Dichloromethane | Report | <100 ppm |
| Tetrahydrofuran | | <100 ppm |
| Acetonitrile | | <100 ppm |
| t-Butyl Methyl Ether | | <100 ppm |
| Potency | Report | 99.6 wt % |

EXAMPLE 3

Preparation of Oleylamide Reference Marker

To a 5-liter flange neck flask fitted with overhead stirrer, temperature probe, nitrogen inlet and a 500 cm$^3$ dropping funnel was charged oleic acid (400.0 g, 1.416 mol) and dichloromethane (3.20 L). The resultant solution was heated to reflux (39-41° C.) and thionyl chloride (202.4 g, 1.2 eq.) added over 10 minutes between 39-41° C.

The reaction mixture was heated at reflux for 3.0 hours, sampling the mixture at hourly intervals (sample quenched into anhydrous methanol, shaken well, and stored at ambient for >1 hour before submitted to analytical development for analysis). The reaction was shown to be 99.9% complete after 3 hours. As the reaction mixture was used in the subsequent amidation reaction without delay, no isomerisation to the trans-isomer was observed.

To a 20-liter flange-neck flask fitted with overhead stirrer, nitrogen inlet, condenser (with silica drying tube) and a gas sparging inlet was charged dichloromethane (12.00 Kg, ~9.1 L). The solvent was cooled to 0-10° C. and then ammonia (960 g) was charged as a gas via the sparging inlet over 140 minutes, maintaining the reaction mixture between 0-10° C. The acid chloride solution in dichloromethane was then added to the stirred ammonia solution via transfer line and 500 cm$^3$ dropping funnel over 32 minutes, maintaining the reaction temperature below 20° C. The resultant pink-coloured suspension was allowed to stir at ambient temperature overnight. A sample was taken (sample quenched into methanol). The reaction mixture was shown to be 76.69% oleylamide and 22.53% oleic acid.

The reaction mixture was quenched by addition of 5M hydrochloric acid solution (8.00 L) over 15 minutes, maintaining the internal temperature of the reaction mixture below 30° C. The quenched mixture was stirred for 10 minutes, transferred to a 20-liter separatory funnel, and allowed to separate (clean separation with good interface achieved). The lower organic layer was removed and retained. The upper aqueous layer was removed and discarded. The dichloromethane solution was then washed with 1M sodium carbonate solution (2×1.60 L). The level of oleic acid was reduced from 24.13% to 13.56% after one wash and to 1.19% after the second wash. The resultant product solution was then washed with water (3×1.60 L) (pH of final wash=8.6) and evaporated to dryness to yield the crude amide as a yellow crystalline solid (284.6 g, 71%).

This material was shown to be 97.41% oleylamide and 1.39% oleic acid by HPLC.

A 25.0 g portion of the batch was recrysllallised from acetonitrile (125 cm³, 5 volumes) to yield 23.8 g purified oleylamide suitable for characterisation as a reference marker. The main characteristics are gathered in Table 2 below:

TABLE 2

Analysis of Oleylamide Reference Marker

| Test | Specification | Result Batch U12543 |
| --- | --- | --- |
| Appearance | Report | Buff powder |
| FT-IR | Conforms to Structure | Conforms |
| $^1$H NMR | Conform to Structure (Report any unknown or unrelated signals) | Conforms |
| $^{13}$C NMR | Conforms to Structure (Report any unknown or unrelated signals) | Conforms |
| Mass Spectrometry | Conforms to formula weight | Conforms |
| Microanalysis (CHN) | Report | 76.84% C (100.05%); 12.60% H (100.56%); 4.84% N (97.19%) |
| Karl Fischer Titration | Report | 0.13% |
| Residual Solvents | | |
| Dichloromethane | Report | <100 ppm |
| Tetrahydrofuran | | <100 ppm |
| Acetonitrile | | <100 ppm |
| TBME | | <100 ppm |
| Sulphated Ash | Report | <0.1% |
| GC (purity) | Report purity | 100.0% |
| Potency | Report | 99.9% |

A new optimised manufacturing method for the production of oleylamine has been developed. Introduction of a purification protocol via oleylamine hydrochloride should ensure that high quality batches of product are consistently produced. In addition, the new process should allow scale-up to larger batch sizes (plant scale permitting) without the proportionate increase in processing time that purification via distillation would dictate.

EXAMPLE 4

Choice of the Extraction-Purification Solvent 0.50 g oleylamine was added to each of three 7 mL sample vials. 2.5 mL (5 volumes) dichloromethane was charged to vial 1. 2.5 mL (5 volumes) toluene was charged to vial 2. 2.5 mL (5 volumes) t-butyl methyl ether was charged to vial 3. 0.185 mL (1.2 molar equivalents) of 37% hydrochloric acid was then charged to all three vials, and the vials were well shaken.

Figure 2:
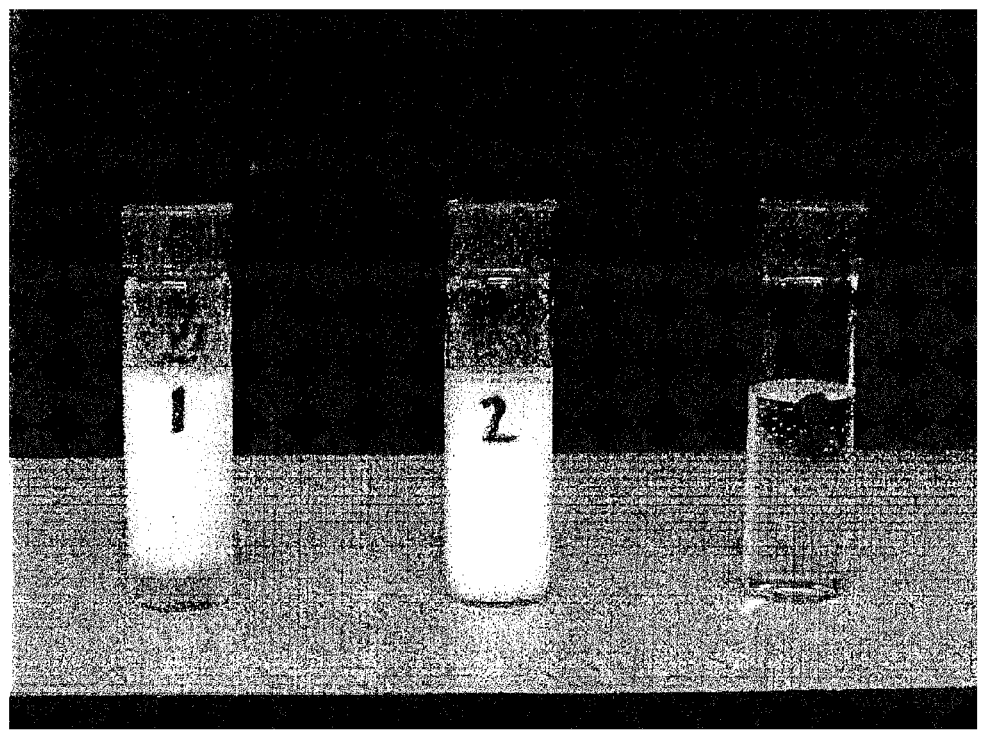
FIG. 2 illustrates the comparison between the clear monophasic solution which is formed when t-butyl methyl ether is used for the purification step d) (vial 3), and the undesirable emulsive mixtures formed when alternative solvents (dichloromethane, vial 1, and toluene, vial 2) are attempted.

The results are illustrated in FIG. 2.

In vials 1 and 2, undesirable emulsions caused by the mixing of the solvent with water supplied by the hydrochloric acid were formed. These emulsions only partly separated upon prolonged standing. However, vial 3 contained a clear monophasic solution. 2 mL water was then charged to all three vials and the contents were well shaken. Vials 1 and 2 gave a cloudy biphasic emulsion, while vial 3 remained a clear monophasic solution. The use of t-butyl methyl ether as solvent leads to a clear monophasic solution, which remains stable upon charging of additional water. Upon addition of this solution to acetonitrile, precipitation of the amine hydrochloride is effectively achieved.

The invention claimed is:

1. A process for the preparation of unsaturated and saturated primary fatty amines comprising the steps of:
   (a) chlorination of the corresponding acid by treatment with neat thionyl chloride in dichloromethane at reflux temperature, to obtain a solution of the corresponding chloride in dichloromethane,
   (b) addition of the chloride solution of step a) to a solution of liquid ammonia in dichloromethane at a temperature comprised between 0 and 10° C. to yield the corresponding amide,
   (c) reduction of the amide to amine by treatment with lithium aluminium hydride in tetrahydrofuran, followed by extraction of amine by t-butyl methyl ether,
   (d) purification of amine of step c) by treatment in solution in t-butyl methyl ether by hydrochloric acid followed by treatment by acetonitrile to yield amine hydrochloride, and optionally
   (e) treatment of amine hydrochloride of step d) by t-butyl methyl ether and a base to yield amine as a free base.

2. The process according to claim 1, wherein the primary saturated and unsaturated fatty amines are selected from the group consisting of amines comprising 4 to 30 carbon atoms, unsaturated amines being allowed to comprise one or more double bonds, isomers and salts thereof.

3. The process according to claim 1, wherein the amines are selected from the group consisting of oleylamine, stearylamine and their respective isomers and salts.

4. The process according to claim 1, wherein the acid used in step a) is oleic acid.

5. The process according to claim 2, wherein the amines are selected from the group consisting of oleylamine, stearylamine and their respective isomers and salts.

6. The process according to claim 2, wherein the amines comprise 15 to 24 carbon atoms.

7. The process according to claim 4, wherein the acid is oleic acid with more than 99% purity.

* * * * *